(12) United States Patent
Schara et al.

(10) Patent No.: US 12,714,289 B2
(45) Date of Patent: Aug. 25, 2026

(54) MEDICAL IMAGING SYSTEM WITH CUSTOMIZABLE PROGRAMMABLE COMMANDS

(71) Applicant: KARL STORZ Imaging, Inc., Goleta, CA (US)

(72) Inventors: Nathan Schara, Washougal, WA (US); Eric Hale, Vancouver, WA (US)

(73) Assignee: KARL STORZ SE & Co. KG, Tuttlingen (DE)

( * ) Notice: Subject to any disclaimer, the term of this patent is extended or adjusted under 35 U.S.C. 154(b) by 26 days.

(21) Appl. No.: 18/667,539

(22) Filed: May 17, 2024

(65) Prior Publication Data

US 2024/0298875 A1 Sep. 12, 2024

Related U.S. Application Data

(63) Continuation of application No. 17/462,348, filed on Aug. 31, 2021, now Pat. No. 12,016,523.

(51) Int. Cl.
*A61B 1/00* (2006.01)

(52) U.S. Cl.
CPC ...... *A61B 1/00042* (2022.02); *A61B 1/00006* (2013.01); *A61B 1/00045* (2013.01)

(58) Field of Classification Search
CPC .. A61B 1/00039–00042; A61B 1/0002; A61B 1/00066; A61B 1/0051; A61B 1/0052; A61B 1/04; A61B 1/045; A61B 1/00006
USPC ................................ 600/118, 103, 131, 160
See application file for complete search history.

(56) References Cited

U.S. PATENT DOCUMENTS 4,880,011 A 11/1989 Imade et al.
5,831,596 A 11/1998 Marshall et al.
2011/0112361 A1 5/2011 Ishigami et al.
2012/0184955 A1* 7/2012 Pivotto .................. A61B 34/30 606/41
2015/0144514 A1 5/2015 Brennan et al.
2016/0199984 A1 7/2016 Lohmeier et al.
2018/0063387 A1 3/2018 Wei et al.
2019/0150723 A1 5/2019 Iwama
2019/0328217 A1* 10/2019 Moreau .................. A61B 1/051
2020/0054403 A1 2/2020 Zhou et al.
(Continued)

FOREIGN PATENT DOCUMENTS

EP 1464918 B1 11/2016
EP 2829846 B1 12/2017

*Primary Examiner* — Ryan N Henderson
*Assistant Examiner* — Pamela F Wu
(74) *Attorney, Agent, or Firm* — David N. Villalpando; Jason Worgull; Jacqueline Cohen

(57) ABSTRACT

A system for controlling a medical imaging scope is disclosed. The system includes a camera head, a display, a processing unit, a memory unit and an input disposed on the medical imaging scope. The processing unit is configured to display a menu that correlates to a plurality of commands. The input is configured to be moveable in three dimensions of space along a set axis, in a plurality of discrete patterns. The processing unit is further configured to associate each of the plurality of discrete patterns with a desired command of the plurality of commands and store each of the plurality of discrete patterns with the desired command of the plurality of commands in the memory unit so as to customize a control of the medical imaging scope.

20 Claims, 5 Drawing Sheets

(56) References Cited

U.S. PATENT DOCUMENTS

| | | | | |
|---|---|---|---|---|
| 2020/0154992 | A1 * | 5/2020 | Zappia, Jr. ......... | A61B 1/00103 |
| 2022/0401166 | A1 * | 12/2022 | Hashimoto ............ | G06N 20/20 |

* cited by examiner

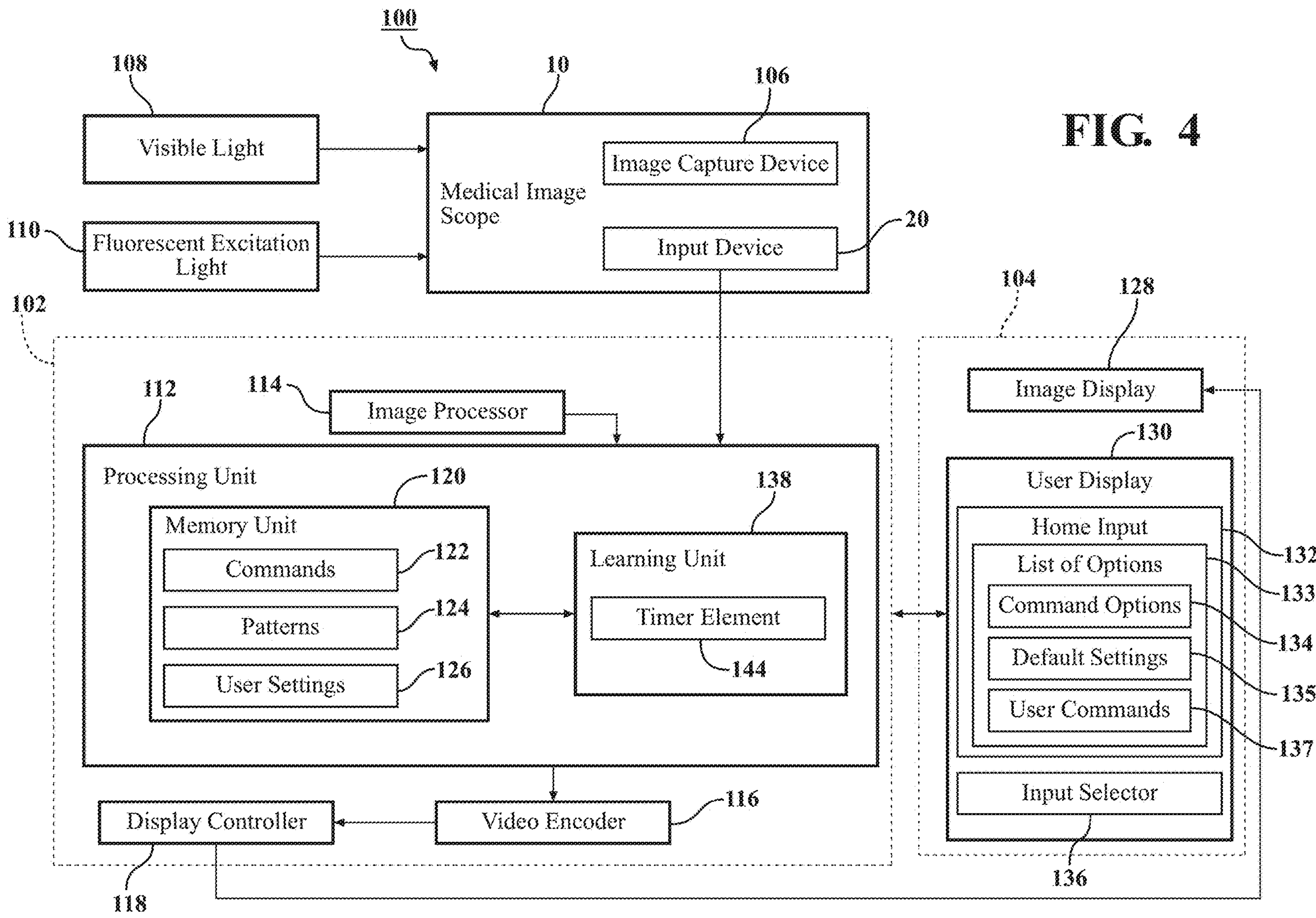
FIG. 4
100
108
Visible Light
110
Fluorescent Excitation Light
10
Medical Image Scope
106
Image Capture Device
Input Device
20
102
104
128
Image Display
112
114
Image Processor
Processing Unit
120
Memory Unit
Commands
122
Patterns
124
User Settings
126
138
Learning Unit
Timer Element
144
130
User Display
Home Input
132
List of Options
133
Command Options
134
Default Settings
135
User Commands
137
Input Selector
136
Display Controller
118
Video Encoder
116

| COMMAND | PATTERN |
| --- | --- |
| Camera Rotation | ↻ |
| Camera Angle | ↗ |
| Switch Light Source | ↳ |
| Picture Capture | ↺ |
| Video View | ↘ |

142 146 148 150 152 140 154 156 158 160

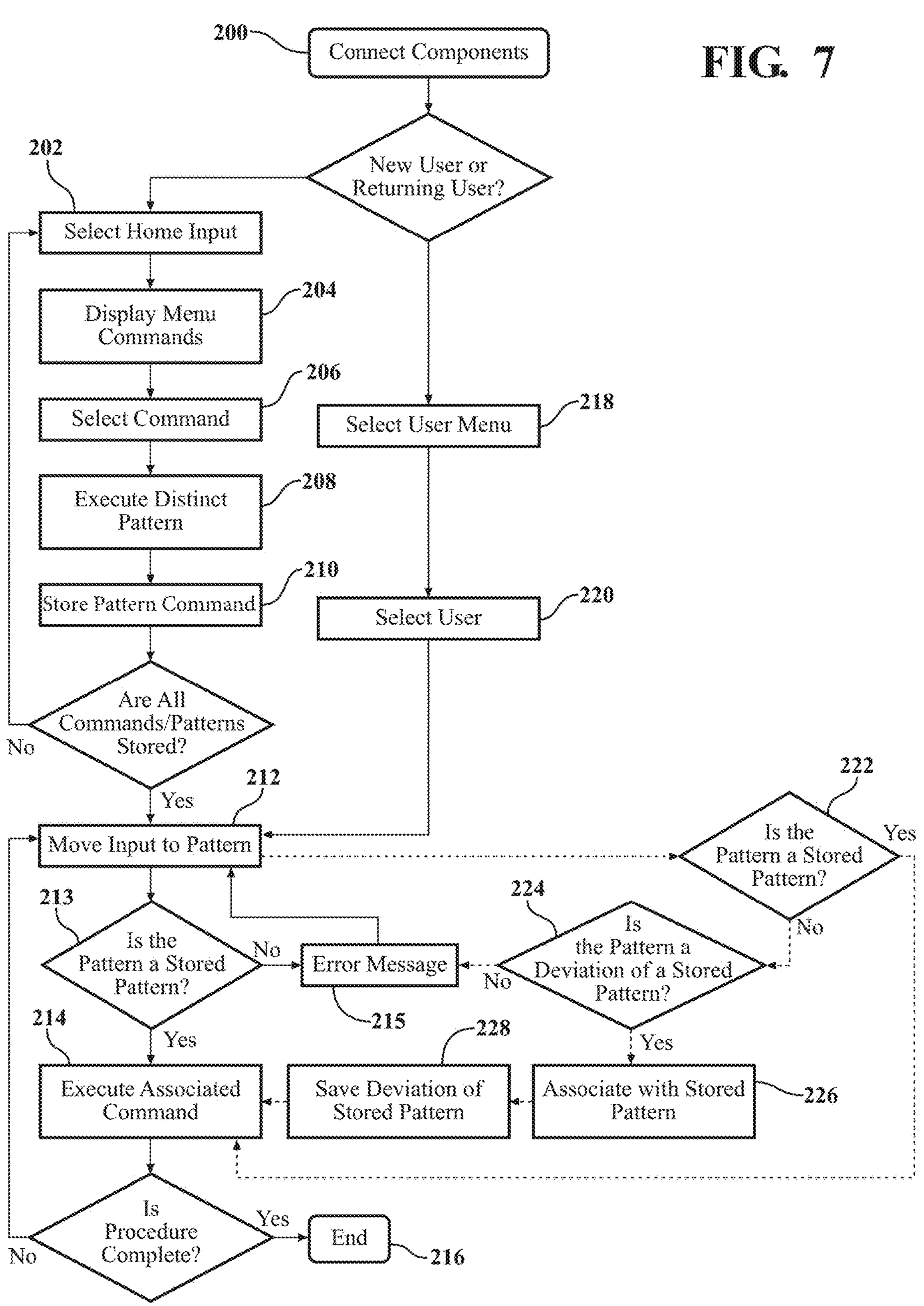
200
Connect Components
FIG. 7
New User or Returning User?
202
Select Home Input
Display Menu Commands
204
Select Command
206
Execute Distinct Pattern
208
Store Pattern Command
210
Select User Menu
218
Select User
220
Are All Commands/Patterns Stored?
No
Yes
212
Move Input to Pattern
222
Is the Pattern a Stored Pattern?
Yes
No
213
Is the Pattern a Stored Pattern?
No
Error Message
215
224
Is the Pattern a Deviation of a Stored Pattern?
No
Yes
214
Execute Associated Command
228
Save Deviation of Stored Pattern
Associate with Stored Pattern
226
Is Procedure Complete?
Yes
No
End
216

MEDICAL IMAGING SYSTEM WITH CUSTOMIZABLE PROGRAMMABLE COMMANDS

CROSS REFERENCE TO RELATED APPLICATIONS

This application is a continuation of U.S. Ser. No. 17/462,348, filed on Aug. 31, 2021, and entitled, "Medical Imaging Scope with Customizable Programmable Commands," Issued as U.S. Pat. No. 12,016,523 on Jun. 25, 2024, which is incorporated herein by reference.

TECHNICAL FIELD

The present disclosure relates generally to the field of medical imaging scopes and more particularly to medical imaging scope arrangements having improved user control of commands.

BACKGROUND

An exemplary prior art medical imaging scope 2 is illustrated in FIG. 1. Medical imaging scope 2 usually includes a first imaging lens (e.g., an objective) followed by a series of carrier lenses (e.g., relays) disposed within an endoscope 5 which capture and transmit an optical image from inside an enclosed area 1 to a camera head 3. A proximal end of the endoscope 5 may be attached, via direct coupling or an adaptor, to the camera head 3 or an eye-piece to allow for viewing. The camera head 3 typically includes an image capture device, such as a CCD or CMOS image sensor, for receiving the optical image and forming a real optical image onto an image sensor. The digital image captured by the image sensor can then be transmitted to a camera control unit (CCU) or other similar module for analysis and display. Typically, two or more buttons 4 that control different aspects of the camera head 3 are positioned on an outer surface of the camera head 3, usually the top surface, though other surfaces have been utilized.

Some endoscope systems have a number of buttons, which are programmed to execute a camera function, for example when the endoscope is used in a different mode or when more complex functions are desired to be controlled easily by the buttons versus other user input which require either the operator moving their hand from the procedure to the system user inputs, or another operator to follow commands from a lead operator.

What is needed are systems and methods that enable a greater number of input movements or gestures, while limiting the number of sensors to detect the movements. In addition, systems and methods that enable customized command actions for a user that would not need visual confirmation of the input selection would be desirable such that the operator would be able to confirm the action to be undertaken without looking at the device and enabling continuous viewing of a display during the procedure.

SUMMARY

One aspect of the disclosure provides a system for controlling an operation of a camera head and the images on a display. The system includes a camera head coupled to the display. The camera head includes a processing unit, a memory unit, and an input device. The processing unit is configured to generate a menu on the display, the menu correlating to a plurality of commands. The input is disposed on the camera head and is configured to be selectively moveable in three dimensions of space along a set axis. The input is further moveable in a plurality of discrete patterns. In one aspect, the system may further include an endoscope disposed on the camera head.

The processing unit is further configured to associate each of the plurality of discrete patterns with a desired command of the plurality of commands and store each of the plurality of discrete patterns with the desired command of the plurality of commands in the memory unit so as to allow for selectively customized control of the endoscope.

In accordance with one aspect of the disclosure, the plurality of commands includes: a camera image rotation; a camera angle; a switch of a light source; a camera zoom, a taking of a picture, and a switch of a video view on the display.

In accordance with another aspect of the disclosure, the system may further include a home input configured to display the menu on the display.

In accordance with another aspect of the disclosure, the menu may further include a list of unique users, wherein each user in the list of users includes the plurality of commands.

In accordance with another aspect of the disclosure, a select input may be provided on the menu. The select input is configured to associate each of the plurality of discrete patterns with a desired command of the plurality of commands.

In accordance with another aspect of the disclosure, the system may further include a learning unit. The learning unit is configured to associate a deviation of one of the plurality of discrete patterns with the desired command of the plurality of commands.

In accordance with another aspect of the disclosure, the input is configured as a joystick. The joystick may be coupled to a magnetometer and/or be rotatable about the set axis. In one exemplary arrangement, the learning unit may store each of the plurality of the discrete patterns and process any change of a magnetic field during operation of the joy stick over a predetermined period of time so as to associate a deviation of each of the plurality of discrete patterns with the desired command of the plurality of commands.

A method of customizing a plurality of commands for use of a camera head is also disclosed. In one exemplary arrangement, the method comprises providing a camera head having a processing unit, providing a memory unit, providing an input disposed on the camera head, where the input is configured to be moveable in three dimensions of space along a set axis, and moving the input in a plurality of discrete patterns and actuating the processing unit to associate each of the plurality of discrete patterns with a desired command of the plurality of commands so as to customize a control of the endoscope. The processing unit may be configured to display a menu, with the menu storing a plurality of commands. In one exemplary method, the plurality of commands includes: rotating a camera image; adjusting a camera angle; switching a light source; change a camera zoom, taking a picture, and switching a video view on a display.

In one exemplary method, the menu further includes a list of users, wherein each user in the list of users includes the plurality of commands.

Another exemplary method includes providing a learning unit. The learning unit associates a deviation of one of the plurality of discrete patterns with the desired command of the plurality of commands.

Another exemplary method provides that the input provided is a joystick, which is coupled to a magnetometer. The method further includes rotating the joystick about the set axis.

In another exemplary method, the deviation detected by the learning unit is a deviation of the discrete patterns in an associated magnetic field over a predetermined time to ascertain which command has been inputted. The learning unit may further store the detected deviation in the memory unit so as to allow for customized control of the endoscope.

In a further exemplary arrangement, a system for selectively controlling and programing of a medical imaging scope is disclosed. The system comprises a camera head, a camera control unit, and a user interface. The camera head is provided with an image capture device. The camera control unit is operatively connected to the camera head and the user interface is operatively connected to the camera control unit. The camera control unit further comprises a processing unit having a memory unit. The processing unit is configured to display a menu on the user interface that correlates to a plurality of commands.

An input disposed on the medical imaging scope. The input is configured to be moveable in three dimensions of space along a set axis, and is selectively movable in a plurality of discrete patterns. The processing unit is further configured to associate each of the plurality of discrete patterns with a desired command of the plurality of commands and store each of the plurality of discrete patterns with the desired command of the plurality of commands in the memory unit so as to customize a control of the medical imaging scope.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

FIG. 4 is block diagram of system utilizing the exemplary medical imaging scope;

FIG. 7 is a flowchart illustrating a method of customizing input commands of a medical imaging scope.

DETAILED DESCRIPTION

A system and method for customizing the operation of a camera head is provided. The system includes a camera head coupled to the display. The camera head includes a processing unit, a memory unit, and an input device. The processing unit is configured to generate a menu on the display, the menu may display a plurality of commands. The input is disposed on the camera head and is configured to be selectively moveable in three dimensions of space along a set axis. The user actuates the input in a plurality of discrete patterns. The processing unit is further configured to associate each of the plurality of discrete patterns with a desired command of the plurality of commands and store each of the plurality of discrete patterns with the desired command of the plurality of commands in the memory unit so as to allow for selectively customized control of the camera head.

Figure 1:
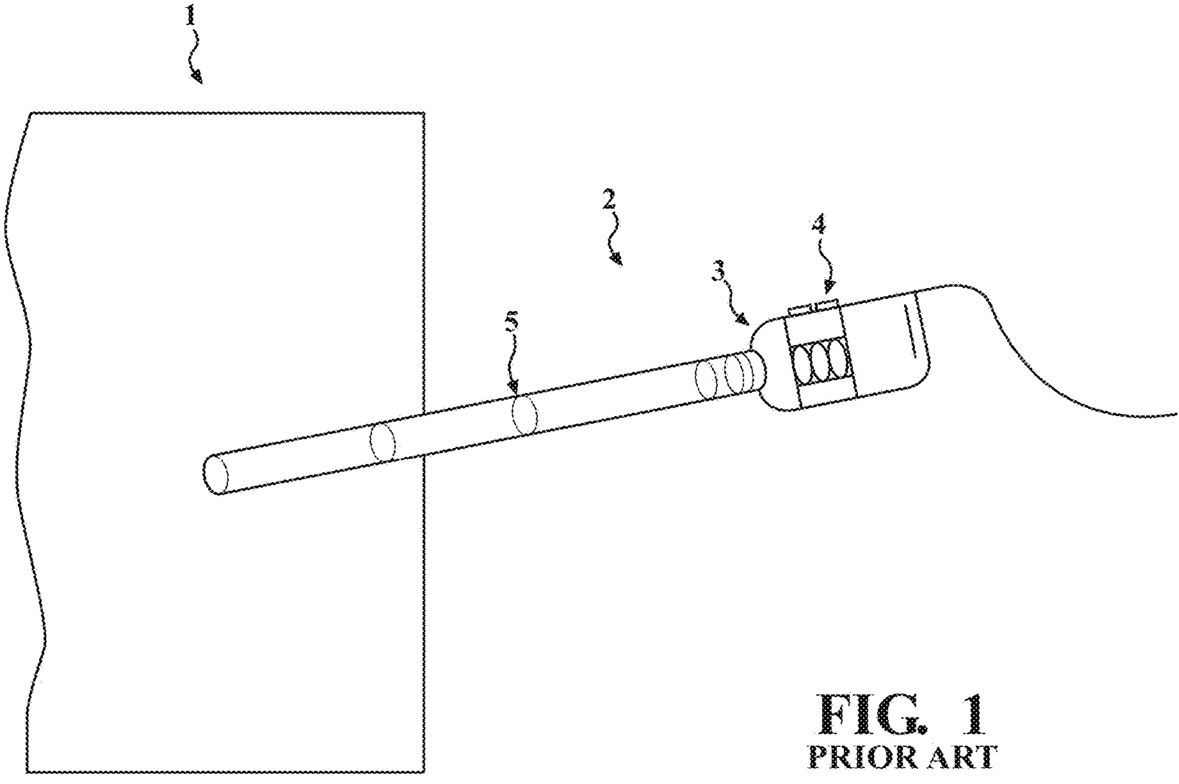
FIG. 1 is an exemplary schematic view of a prior art medical imaging scope.
Figure 2:
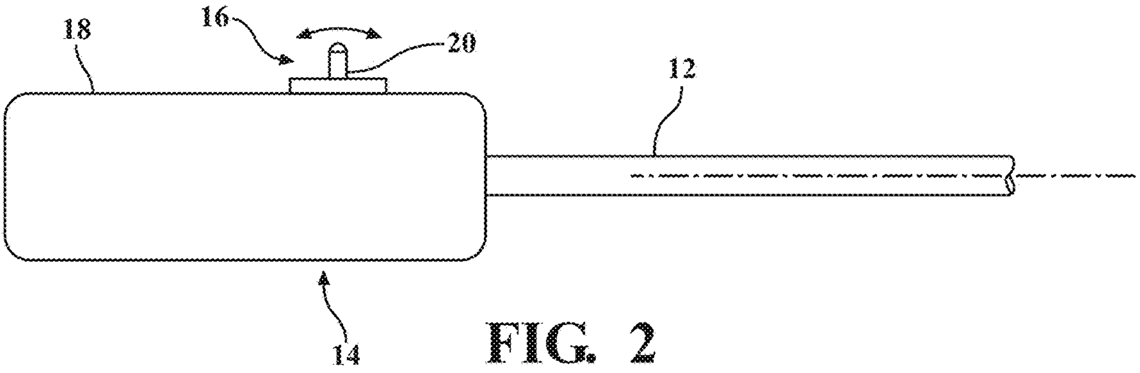
FIG. 2 is an exemplary medical imaging scope in accordance with the current disclosure.

With reference now to the Figures, a system for customizing the operation of a camera head is provided. An exemplary medical imaging scope 10 is illustrated in FIG. 2. The medical imaging scope 10 comprises an endoscope 12 extending from a camera head 14. An input device 16 is mounted to the camera head 14. In one exemplary arrangement, the input device 16 is mounted so as to extend through a top surface 18 of the camera head 14. This configuration will assist in orienting the endoscope 12, as well as providing ready visual and tactile indication of the location of the input device 16. In one exemplary arrangement, the input device 16 is a joystick 20 that permits a variety of movement about an axis.

Figure 3:
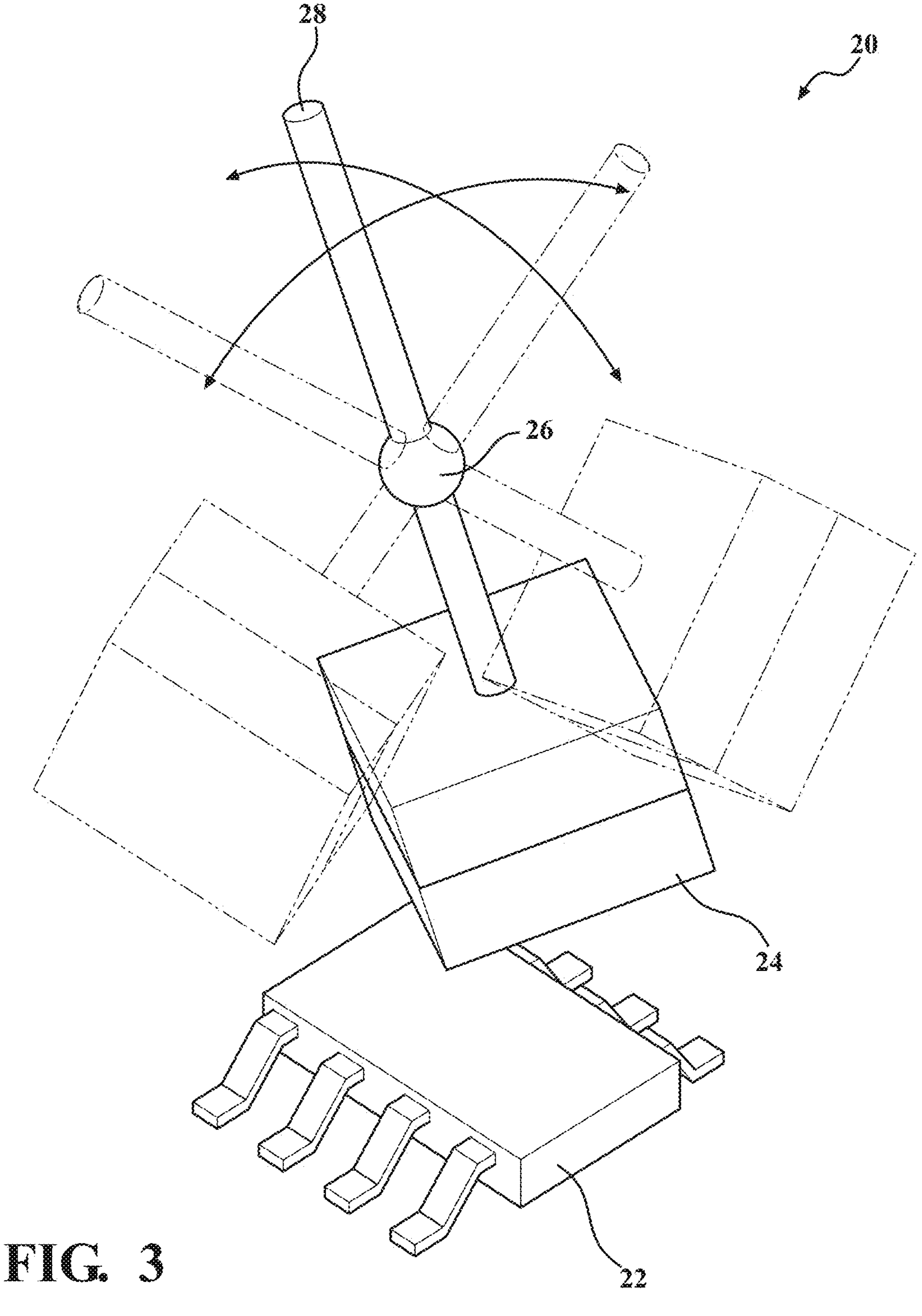
FIG. 3 is an exemplary representative view of an input device for use with a camera head of the medical imaging scope.

Referring to FIG. 3, a configuration of an input arrangement utilizing a joystick 20 is shown in greater detail. More specifically, a magnetometer 22 is positioned within a housing **14*a* of the camera head 14. The joystick 20 is coupled to a magnet 24, which is also positioned within the housing 14*a*. The joystick 20 further comprises a ball joint mechanism 26 to which an input shaft 28 is attached. A portion of the input shaft 28 is located outside of the housing 14*a*, as shown in FIG. 2. The ball joint mechanism 26 is rotatably seated within the housing 14*a* and allows for tilting the ball joint mechanism 26 about the housing 14*a* in any angular direction about an XY plane and with various angles from an upright Z axis. Further, the disclosure contemplates that the joystick 20 may even be pressed or rotated about the Z axis as well. As the joystick 20 is moved in various directions, the movement is detected by the magnetometer 22**.

Although input device 16 refers to a joystick 20, one skilled in the art would recognize that other features may be used to manipulate the input shaft 28. For example, a control pad similar to known camera head configurations with "up," "down," "left," and "right" buttons could engage the shaft 28 to move the magnet 24 in a similar fashion as a joystick. Likewise, a circular, single button centered atop the shaft 28 could move the magnet 24 about the ball joint mechanism 26. Although a magnet 24 and magnetometer 22 are shown, other sensors or combinations could be used such as a magnetic imaging sensor.

Referring to FIG. 4, a system hardware block diagram of an exemplary system 100 for use with the medical imaging scope 10 is shown. The system 100 includes a camera control unit 102 and a user interface 104, which may include one or more displays 128, 130. For example, in one exemplary arrangement, there may be an image display 128 that displays the images captured by the camera head 14 and a separate user display 130 where the user may navigate between a list 132 of different operating options for the system 100, as will be explained in further detail below. However, it is also understood that the system 100 may include a single display 128 that is capable of being used for both displaying images and navigation through the system 100 options.

The system 100 further includes the medical imaging scope 10 described above. The medical imaging scope 10 includes the camera head 14 having an image capture device 106, such as a CCD or CMOS image sensor. In one exemplary configuration, the medical imaging scope 10 may be a dual mode visible light and fluorescence imaging device, wherein a visible light source 108 and a fluorescent excitation light source 110 are provided to illuminate the image captured by the image capture device 106. However, it is understood the scope of the disclosure is not limited to such a medical imaging scope and that the features and methods disclosed herein may be employed with various medical imaging scopes, including visible light only scopes. In the representative medical imaging scope 10, the camera head 14 is integrated with the endoscope 12. The optical assembly includes at least one lens, which may be a wide angle lens element such that the optical assembly is capable of focusing light that represents a wide field of view. It is also understood that the disclosure is applicable to more than one type of device enabled for image capture, such as endoscopes, video scopes, flexible endoscopes, other medical imaging devices, and digital microscopes, for example.

The medical imaging scope 10 further includes an input device, which may be the joystick 20 discussed above. For example, and as will be explained in further detail below, in one exemplary arrangement, the input device may include the magnet 24 which allows for the input of different patterns to be utilized for executing commands by utilizing a change to a local magnetic field that is detected by the magnetometer 22.

The camera control unit 102 of system 100 controls the overall operation of the camera head 14 and further includes a processing unit 112 and an image processor 114. The camera control unit 102 may be integrated with the camera head 14 or remote therefrom. The image processor 114 performs digital image processing functions to process and filter the received image stream from the camera head 14 as is known in the art. In addition, the camera control unit 102 may further include a video encoder 116 and a display controller 118. The processing unit 112 further comprises a memory unit 120. As will be explained in further detail below, the memory unit 120 stores a plurality of commands 122 for the medical imaging scope 10. In addition, the memory unit 120 further stores different patterns 124 that the input device 20 may execute to effect specific commands. The processing unit 112 correlates a unique command 122 with a discrete pattern 124 to operate the medical imaging scope 10. In one exemplary arrangement, the memory unit 120 can also store different user settings 126. For example, and as will be explained in further details below, each user can customize movement patterns that are unique for each user, where the movement patterns correlate to distinct commands. Multiple user profiles may be stored which include each user's discrete patterns and respective unique commands 124.

In one exemplary arrangement, the user interface 104 includes an image display 128 and a user display 130. In addition, it is understood that other displays may also be included, as well as a keyboard or other selection device (stylus, mouse, etc.). The image display 128 receives images taken by the camera head 14 and transmitted through the camera control unit 102, and specifically to the video encoder 116 and to the display controller 118.

As will be explained below, incorporation of the joystick 20 with the magnetometer 22 allows for numerous patterns to be created for different actions. Moreover, the system 100 allows for each user to define any pattern created by the joystick 20 for a given command. The pattern may include a continuous motion of the joystick 20 over a predetermined time. Further, system 100 allows for slight deviations of an executed pattern to be detected as an intended command.

The user display 130 is operatively connected to the processing unit 112. The user display 130 may include a menu 132. The menu 132 may be a home input icon that is configured to display a list of one or more options 133 for a user to select from during operation of the system 100. The list 133 includes a menu of commands 134 that the medical image scope 10 can perform. In addition, the user display 130 may have an input selector 136 that allows a user to input and save data into the system 100. In another exemplary arrangement, the system 100 may be provided with a pre-programmed menu of default settings 135 that include set commands that are associated with pre-programmed specific patterns in the memory unit 120 that a user can immediately use. Thus, the user display 130 may be programmed to allow a user to select the "default" setting 135 option from a list of options 133, which correlates to a menu of pre-stored commands with pre-stored discrete input patterns stored in the memory unit 120 of the system 100. Thus, as one example, if it is desired to zoom in the camera view, the pre-program pattern may be in the configuration of a simply forward push of the joystick 20. The user then manipulates the joystick 20, by pushing the joystick 20 forward, thereby zooming in the image.

As a further exemplary arrangement, the system 100 may allow users to set their own unique patterns for executing certain commands and save those associated patterns and commands in the memory unit 120. Further, the system 100 may also be configured to save the unique patterns for the commands by user in the memory unit 120. In this instance, the list 133 in the home input 132 may be programmed to allow a user to select between different "user commands" options 137 for the system 100 for which the memory unit 120 has stored commands and discrete patterns unique to each user or provide an option to add additional users. In addition, the input selector 136 allows a user to input user data, including an option to save unique command and discrete patterns for additional users or change command/pattern options for established users, such as a "program command" option. Once selected, the system 100 may provide an "execute pattern" input, followed by a "save pattern" option. Thus system 100 allows users to create their own customized commands based upon movement that are inherent to the user.

Figures 5, 6:
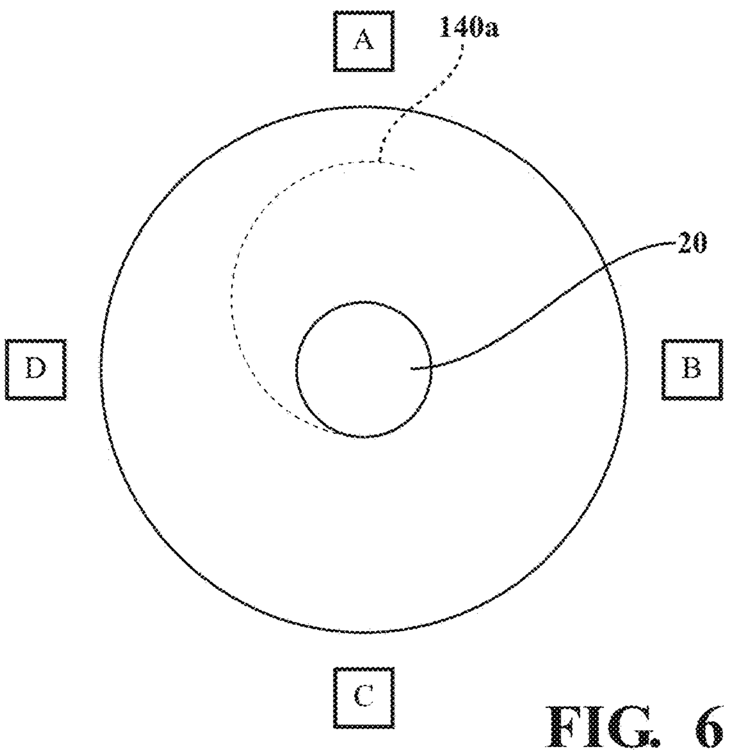
FIG. 5 is an exemplary menu of potential input patterns than may be associated with commands.
FIG. 6 is a plan view of a representative input pattern.

The processing unit 112 may further include a learning unit 138. The learning unit 138 is configured to associate a deviation of one of the discrete patterns that is stored in the memory unit (whether a default setting or a user defined setting) and associate that deviated discrete pattern with a desired command from the plurality of commands. For example, referring to the table of exemplary commands and patterns in FIG. 5, a discrete movement such as forming a C-shape pattern 140 is accomplished by rotating the joystick 20. The pattern 140 is then detected by the magnetometer 22 (and more specifically a detection of the change of a magnetic field) and captured for a first user for the command camera rotation 142 by the camera head 14 by the user actuating the input selector 136. During use of the system 100, however, the user may execute a movement of the joystick 20 that does not exactly match the captured C-shape pattern 140, but instead deviates from the captured discrete pattern 140 by a predetermined amount. For example, in one exemplary embodiment, referring to FIG. 6, if rotation of the joy stick 20 extends past the D and A points and traverses approximately 90% of the captured C-shape pattern 140', as represented by the dotted lines, the learning unit 138 is configured to recognize the pattern 140' as intending to replicate pattern 140 and shall also associate the deviated pattern 140' with the camera rotation command and save that action in the memory unit 120. It is understood that the learning unit 138 may be programmed with a threshold range of deviation. In one exemplary arrangement the range of deviation that the learning unit 138 may recognize as one of a discrete commands is between 80-100% of the discrete patterns. For example, a preset margin of error based on a preprogramed range or deviation or a learned margin of error based on repetitive input and learning may be used to determine when only a slight deviation from an ideal pattern is detected, such as one that includes an error less than the preset margin of error, and thus the intended command is known.

In accordance with another potential arrangement, the learning unit 138 may further include a time element 144 therein. The time element 144 is configured to capture an executed discrete pattern with a predetermined time range. More specifically, if a user begins to execute one of the discrete patterns, but pauses the movement before completion of the pattern, and if the movement is resumed and completed within the predetermined time range set by the time element 144, the learning unit 138 will still recognize the pattern and associate it with the corresponding command. However, if the pause exceeds the predetermined time range, an error message may be communicated to the user display 130 to alert the user.

It should be appreciated that the learning unit 138 may be a neural network that is trained to determine a desired command with a pattern executed by the joystick. The learning unit may be trained by including multiple joystick inputs attempting to execute the same pattern. Some amount of tolerance and deviation from the pattern may be considered by the learning unit 138 as acceptable or within range to correlate to the desired command, thus, allowing for tolerance and deviation in the patterns of an actuated joystick to correlate with the desired command.

It is understood that any number of associated commands and patterns may be captured in the memory unit 120. Representative commands additionally include, but are not limited to, changing the camera angle 146, switching the light source 148, capturing the picture 150 and changing the video view 152. Representative discrete patterns that may be detected additionally include, but are not limited to a V-shaped pattern 154, an L-shaped pattern 156, a P-shaped pattern 158 and a side-ways V-shape pattern 160. In one exemplary arrangement, the V-shaped pattern 154 is associated with the change of camera angle command 146, the L-shaped pattern 156 is associated with switching the light source command 148, the P-shaped pattern 158 is associated with capturing the picture command 150, and the side-ways V-shape pattern 160 is associated with changing the video view command 152.

Referring to FIG. 7, a flow chart illustrates a method of customizing a plurality of commands of a medical imaging scope 10. The method begins in block 200 by connecting the medical imaging scope 10 or other medical scope having an input 20 that is configured to move in discrete patterns to a camera control unit 102 and connecting the camera control unit 102 to a user interface 104. After the medical imaging scope 10 is connected and powered on, for a new user, the new user will proceed to block 202 and select the home input 132 option to program the system 100. As discussed above, the home input 132 may be displayed on a display 130 and a user input device, such as a stylus (if the display is configured as a touch screen), a keyboard or mouse, may be utilized to select the home input 132.

The method will then proceed to block 204, where a menu 134 of a variety of command options will appear. The user then selects or inputs a command, for example, rotating the camera image 142 at block 206. Once the command is determined, the user may then initiate a "program command" option on the display 128 and an "execute pattern" option. Then the user manipulates the input to execute a discrete pattern, such as, for example the C-shaped pattern 140, at block 208. Once the pattern is executed, the user then selects the input selector 136 to capture the discrete pattern, thereby associating the discrete pattern with the desired command, and store the associated discrete pattern/command in the memory unit 120 at block 210. The input selector 136 may also allow for storing the associated discrete pattern/command to a specific user at block 210. The method will repeat steps 202-210 until all desired commands and associated discrete patterns are captured and stored in the memory unit 120 and associated with a specific user. Once all of the discrete patterns and associated commands are stored, the method proceeds to block 212 whereby the user moves the input in a pattern. The method then proceeds to block 213, whereby the processing unit 112 determines if the pattern is a stored pattern. If the pattern is a stored pattern, the method proceeds to block 214 and correlates the stored pattern with its associated command to operate the medical imaging scope 10 to execute the desired command. This method continues until all the commands for the procedure are completed. Once the procedure is completed, the method ends at block 216.

If it is determined at block 213 that the pattern is not a stored pattern, in one exemplary arrangement, the method proceeds to block 215. At block 215 an error message is sent to the user display 130. Alternatively, if it is determined that the pattern is not a stored pattern, the medical imaging scope 10 can remain inoperable until an executed pattern is recognized. The method then returns to block 212.

For returning users, after block 202, the user will proceed to block 218 and select the user commands menu 137 from the user interface 104. "Default settings" 135 may be considered a returning user for purposes of the method described. Once the menu of user commands appears, the user selects his/her name or other identification (i.e., employee number) from the user commands menu 137 in block 220. The user's pre-stored discrete patterns and associated commands are accessed from the memory unit 120 and available for use by the user. The method then proceeds to block 212.

In one exemplary method, the processing unit 112 may further include the learning unit 138 that is capable of recognizing deviations from the distinct patterns that are stored in the memory unit 120 and associating those deviations with the desired command. In such arrangements, as represented by dotted lines, in block 222, the processing unit 112 determines if the pattern executed by the user is one of the discrete patterns stored in the memory unit 120. If yes, the method proceeds to block 214 as outlined above. However, if the pattern executed is not one that is stored, the method proceeds to block 224.

At block 224, the learning unit 138 determines if the pattern executed is a deviation of a stored pattern. More specifically, the leaning unit 138 determines if the pattern executed is similar to a stored pattern above a predetermined threshold. If the pattern executed is similar to the stored pattern above the predetermined threshold, in block 226, the learning unit 138 associates this deviation of a stored pattern with the command of the stored pattern. In block 228, the deviation of the stored pattern is also saved in the memory unit 120. The method then returns to block 214.

If the deviation of the pattern executed exceeds the predetermined threshold, the method will proceed to block 215.

In one exemplary method, the learning unit 138 may also be provided with the time element 144. At block 222, the determination of whether the pattern executed based on a predetermined time limit for the execution of the pattern.

A number of implementations have been described. Nevertheless, it will be understood that various modifications may be made without departing from the spirit and scope of the disclosure. Accordingly, other implementations are within the scope of the following claims.

The invention claimed is:

1. A system for controlling a medical imaging scope comprising:

a camera head comprising a housing;

a display;

a processing unit configured to display a menu, the menu correlating to a plurality of commands, the processing unit having a memory unit;

a joystick configured to be movable in three dimensions of space along a set axis, the joystick disposed on the medical imaging scope external to the camera head housing, wherein the joystick is positioned atop an input shaft, the input shaft extending from the joystick into the housing and coupled to a magnet within the housing, the joystick configured to be engaged in in a plurality of discrete patterns; and wherein the processing unit is further configured to associate each of the plurality of discrete patterns with a desired command of the plurality of commands, each of the plurality of commands being one of a plurality of camera functions and store each of the plurality of discrete patterns with the desired command of the plurality of commands in the memory unit so as to customize a control of the medical imaging scope.

2. The system as set forth in claim 1, wherein the plurality of commands includes: a camera image rotation; a camera angle; a switch of a light source; a camera zoom; a taking of a picture; and a switch of a video view on the display.

3. The system as set forth in claim 2, wherein the menu further includes a list of users, wherein each user in the list of users includes the plurality of commands.

4. The system as set forth in claim 3, further including a select input, the select input is configured to associate each of the plurality of discrete patterns with a desired command of the plurality of commands.

5. The system as set forth in claim 4, further including a learning unit, the learning unit configured to associate a deviation of one of the plurality of discrete patterns with the desired command of the plurality of commands.

6. The system as set forth in claim 1, further including a home input, the home input configured to display the menu on the display.

7. The system as set forth in claim 1, wherein the camera head further comprises a magnetometer positioned within the housing and configured to detect the position of the magnet.

8. The system as set forth in claim 7, wherein the joystick is rotatable about the set axis.

9. The system as set forth in claim 8, wherein the menu further includes a list of users, wherein each user in the list of users includes the plurality of commands.

10. The system as set forth in claim 7, further including a learning unit, the learning unit storing each of the plurality of discrete patterns and processing a change of a magnetic field over a predetermined period of time so as to associate a deviation of each of the plurality of discrete patterns with the desired command of the plurality of commands.

11. A method of customizing a plurality of commands of a camera head, the method comprising:

providing a processing unit configured to display a menu, the menu storing a plurality of commands, the processing unit including a memory unit;

providing a joystick positioned atop an input shaft, the input shaft extending from the joystick through a housing of the camera head and coupled to a magnet within the housing, the joystick disposed on the camera head, and configured to be engaged in a plurality of distinct patterns; and moving the joystick in any number of the plurality of discrete patterns and actuating the processing unit to associate each of the plurality of discrete patterns with a desired command of the plurality of commands so as to customize a control of the camera head, wherein each of the plurality of commands is one of a plurality of camera functions.

12. The method as set forth in claim 11, wherein the plurality of commands includes: rotating a camera image; changing a camera angle; switching a light source; changing a camera zoom; taking a picture; and switching of a video view on a display.

13. The method as set forth in claim 12, wherein the menu further includes a list of users, wherein each user in the list of users includes the plurality of commands.

14. The method as set forth in claim 13, further including providing a learning unit, the learning unit configured to associate a deviation of one of the plurality of discrete patterns with the desired command of the plurality of commands.

15. The method as set forth in claim 14, wherein engaging the joystick includes rotating the joystick about the set axis.

16. The method as set forth in claim 14, wherein the deviation is a deviation of a magnetic field over a predetermined period of time detected by a magnetometer.

17. The method as set forth in claim 11, wherein the joystick is coupled by means of the input shaft to a magnetometer.

18. A system for controlling a medical imaging scope comprising:

a camera head comprising a housing and a magnetometer positioned within the housing;

a display;

a processing unit configured to display a menu, the menu correlating to a plurality of commands, the processing unit having a memory unit;

an input device disposed on the medical imaging scope external to the camera head housing, the input device selected from the group consisting of a joystick, a control pad, and a circular, single button, wherein the input device is positioned atop an input shaft and is configured to be movable in three dimensions of space along a set axis and to be rotatable about the axis, the input shaft extending from the input device into the housing and coupled to a magnet within the housing, the input device configured to be engaged in in a plurality of discrete patterns; and wherein the magnetometer is configured to detect the position of the magnet, and wherein the processing unit is further configured to associate each of the plurality of discrete patterns with a desired command of the plurality of commands, each of the plurality of commands being one of a plurality of camera functions and store each of the plurality of discrete patterns with the desired command of the plurality of commands in the memory unit so as to customize a control of the medical imaging scope.

19. The system as set forth in claim 18, wherein the menu further includes a list of users, wherein each user in the list of users includes the plurality of commands.

20. The system as set forth in claim 18, further including a select input, the select input is configured to associate each of the plurality of discrete patterns with a desired command of the plurality of commands.

* * * * *